United States Patent
Haumann et al.

(10) Patent No.: US 6,201,983 B1
(45) Date of Patent: Mar. 13, 2001

(54) COMBINED POWER AND DATA TRANSMISSION ARRANGEMENT ACCOMMODATING ALL ELECTRICAL NEEDS OF A NUMBER OF INDEPENDENTLY OPERABLE MEDICAL APPARATUSES IN A MEDICAL WORKSTATION

(75) Inventors: Hans-Juergen Haumann, Erlangen; Klaus Herrmann, Nuremberg; Heinz Weimar, Baiersdorf, all of (DE)

(73) Assignee: Siemens Aktiengesellschaft, Munich (DE)

( * ) Notice: Subject to any disclaimer, the term of this patent is extended or adjusted under 35 U.S.C. 154(b) by 0 days.

(21) Appl. No.: 09/234,206

(22) Filed: Jan. 20, 1999

(30) Foreign Application Priority Data

Jan. 22, 1998 (DE) ................................. 198 02 340

(51) Int. Cl.⁷ ........................... G06F 17/00; A61B 10/00
(52) U.S. Cl. .......................................... 600/407; 128/920
(58) Field of Search ..................... 600/109, 112, 600/160, 166, 132, 407, 411, 427, 437, 439; 601/2–4; 128/920; 378/62–65, 37; 250/370.08, 370.09; 606/180

(56) References Cited

U.S. PATENT DOCUMENTS

| 5,081,984 | * | 1/1992 | Wess et al. ........................ 601/4 |
| 5,400,792 | | 3/1995 | Hoebel et al. . |
| 5,488,951 | | 2/1996 | Bauer et al. . |
| 5,553,618 | * | 9/1996 | Suzuki et al. ..................... 601/3 |
| 5,664,570 | * | 9/1997 | Bishop .............................. 601/2 |
| 5,740,801 | * | 4/1998 | Branson ........................ 600/407 |
| 5,878,746 | * | 3/1999 | Lemelson et al. ............. 128/920 |
| 5,885,214 | * | 3/1999 | Monroe et al. ................ 600/407 |

FOREIGN PATENT DOCUMENTS

19700270 * 1/1997 (DE) .

OTHER PUBLICATIONS

HP Manual "Your Guide to Setting up Your LaserJet III Printer, "(Feb., 1990).

* cited by examiner

Primary Examiner—Joseph Pelham
(74) Attorney, Agent, or Firm—Schiff Hardin & Waite

(57) ABSTRACT

An apparatus system has a connection unit and a number of apparatuses which can be connected to the connection unit and can be operated as intended independently of one another and independently of the connection unit. Each apparatus has a system lead including a number of connecting cables connected to a system connector and the connection unit having plug devices for the system connectors for the purpose of connecting the apparatuses to the connection unit. All the electrical connecting cables required to operate an apparatus in each case are combined in the system lead of the apparatus.

5 Claims, 3 Drawing Sheets

COMBINED POWER AND DATA TRANSMISSION ARRANGEMENT ACCOMMODATING ALL ELECTRICAL NEEDS OF A NUMBER OF INDEPENDENTLY OPERABLE MEDICAL APPARATUSES IN A MEDICAL WORKSTATION

BACKGROUND OF THE INVENTION

1. Field of the Invention

The invention relates to an apparatus system, for example of a group of medical apparatuses which together form a medical workstation.

2. Description of the Prior Art

A medical apparatus system of the above type includes, for example, a patient supporting table, an X-ray apparatus, a diagnostic ultrasound apparatus and a lithotripter having a shock wave source, which form a workstation for the treatment of patients suffering from calculi, for example kidney stones. As a rule, the apparatuses of the medical apparatus system, which are individually known, can be operated completely independently of one another and are separately designed, that is to say each of the apparatuses has, for example, a dedicated housing or a dedicated apparatus trolley with dedicated data and power supply cables, dedicated control and further items of equipment for operating the apparatus. Under certain circumstances, the individual apparatuses can be mechanically coupled to one another, at least in part, in the course of forming a workstation, as described for a lithotripter and a C-arm X-ray apparatus in European application 606 548.

The separately designed apparatuses forming a workstation must, for some treatments, be able to exchange data with one another. For example, when the focus of the shock wave source of the lithotripter is aligned with a kidney stone to be disintegrated in the patient's body between the lithotripter, the diagnostic ultrasound apparatus, the patient supporting table and the X-ray apparatus, these apparatuses must be electrically connected to one another via corresponding connecting cables. As a rule, two connecting cables are in each case necessary between two apparatuses for the data exchange between the two apparatuses. The apparatuses are supplied with power independently of one another by corresponding power supply cables which connect the individual apparatuses to respective power sources.

The manual "Your Guide to Setting Up Your LaserJet III Printer" from the company Hewlett Packard dated February, 1990 with the printing record 33449-90933 describes the connection of a printer to a personal computer PC. The PC and the printer in this case form an apparatus system, the data exchange between the PC and the printer being carried out via a serial or parallel interface. The apparatuses are supplied with power independently of one another via separate power supply cables.

It proves to be disadvantageous that the electrical connections of the individual apparatuses to one another for the purpose of data exchange and the electrical connections of the individual apparatuses to power sources for the purpose of power supply require a multiplicity of connecting cables, which complicate the connection of the apparatuses to form an apparatus system and expose personnel working on the apparatus system to the constant risk of tripping over them.

SUMMARY OF THE INVENTION

An object of the present invention is to provide an apparatus system of the type mentioned in the introduction wherein the connection of the apparatuses to one another for the purpose of common data exchange and the power supply of the apparatuses are simplified.

This object is achieved according to the invention in an apparatus system having a connection unit and apparatuses which can be connected to the connection unit and can be operated as intended independently of one another and independently of the connection unit. Each apparatus has a system lead including a number of connecting cables connected to a system connector and the connection unit having plug devices for the system connectors for the purpose of connecting the apparatuses to the connection unit. All the electrical connecting cables required to operate an apparatus in each case are combined in the system lead of the apparatus. The system lead serves for connecting the apparatus to the connection unit, which has corresponding plug devices for the system connectors for the purpose of connecting the apparatuses. In this case, the connection unit preferably has means which enable and/or control the data exchange between the individual apparatuses of the apparatus system via the system leads while also ensuring that the apparatuses of the apparatus system are supplied with power via the system leads. In this way, the connection of apparatuses to form an apparatus system is considerably simplified since each apparatus which is intended to be part of the apparatus system only has to be connected by one system lead to the connection unit, via which the apparatus is supplied with power and via which data is exchanged between the apparatus and other apparatuses. In this case, in accordance with one version of the invention, the system lead of an apparatus includes data and/or video and/or power supply cables. Therefore, in the case of the apparatus system according to the invention, the number of free electrical connecting cables of the apparatus system also can be considerably reduced, thereby reducing the risk to personnel of tripping over connecting cables which are lying around.

In order to enable operation of the apparatus of the apparatus system as intended independently of the connection unit, the apparatuses may have, an addition to the system lead, for example a separate power supply cable and also/or else other connecting cables which are necessary for the operation of the respective apparatus. These connecting cables, however, are required only for so-called stand-alone operation of the apparatuses, that is to say for the operation of the respective apparatus independently of the connection unit and/or the apparatus system. It is thus possible for an apparatus to have, for example, a power supply cable integrated in the system lead and, in addition, a separate power supply cable. The connecting cables which are not needed are in this case temporarily stored in the respective apparatus in such a way that they do not have a disruptive effect.

In another embodiment of the invention the system leads and system connectors of the apparatuses and also the plug devices of the connection unit each has an identical design. The identical embodiment has the advantage that the system leads, connectors and plug devices are, as a rule, inexpensive to produce on account of higher numbers. This identical design embodiment, however, makes it necessary to identify an apparatus which is connected to an arbitrary plug device of the connection unit, for example in order to set up a data exchange between two apparatuses. Therefore, the system connectors and leads of the different apparatuses and also the plug devices of the connection unit for the system connectors of the apparatuses may also be of different designs, the different design embodiment having the advantage that the identification of an apparatus by the connection unit is simple, although the production of the system leads, connectors and plug devices is more expensive. In both cases, the connection unit preferably has means which are able to identify an apparatus connected to the Connection unit in accordance with the plug play principle.

In a further version of the invention the connection unit has at least one communications bus, to which, for example, the data cables of the system leads and/or the corresponding connections of the system connectors and/or plug devices are connected. The data exchange between the apparatuses connected to the connection unit can thus take place in an advantageous manner via the communications bus. The connection unit can have at least one control computer, which is preferably connected to the communications bus. In this way, it is possible for the control computer to control the data exchange between the apparatuses of the apparatus system via the communications bus, or to make the control computer superordinate to the controllers of the apparatuses, thereby enabling the apparatus system to be controlled centrally from the control computer. Such a control computer may be, for example, a personal computer (PC) having corresponding control, input/output and memory modules.

DESCRIPTION OF THE PREFERRED EMBODIMENTS

Figure 1:
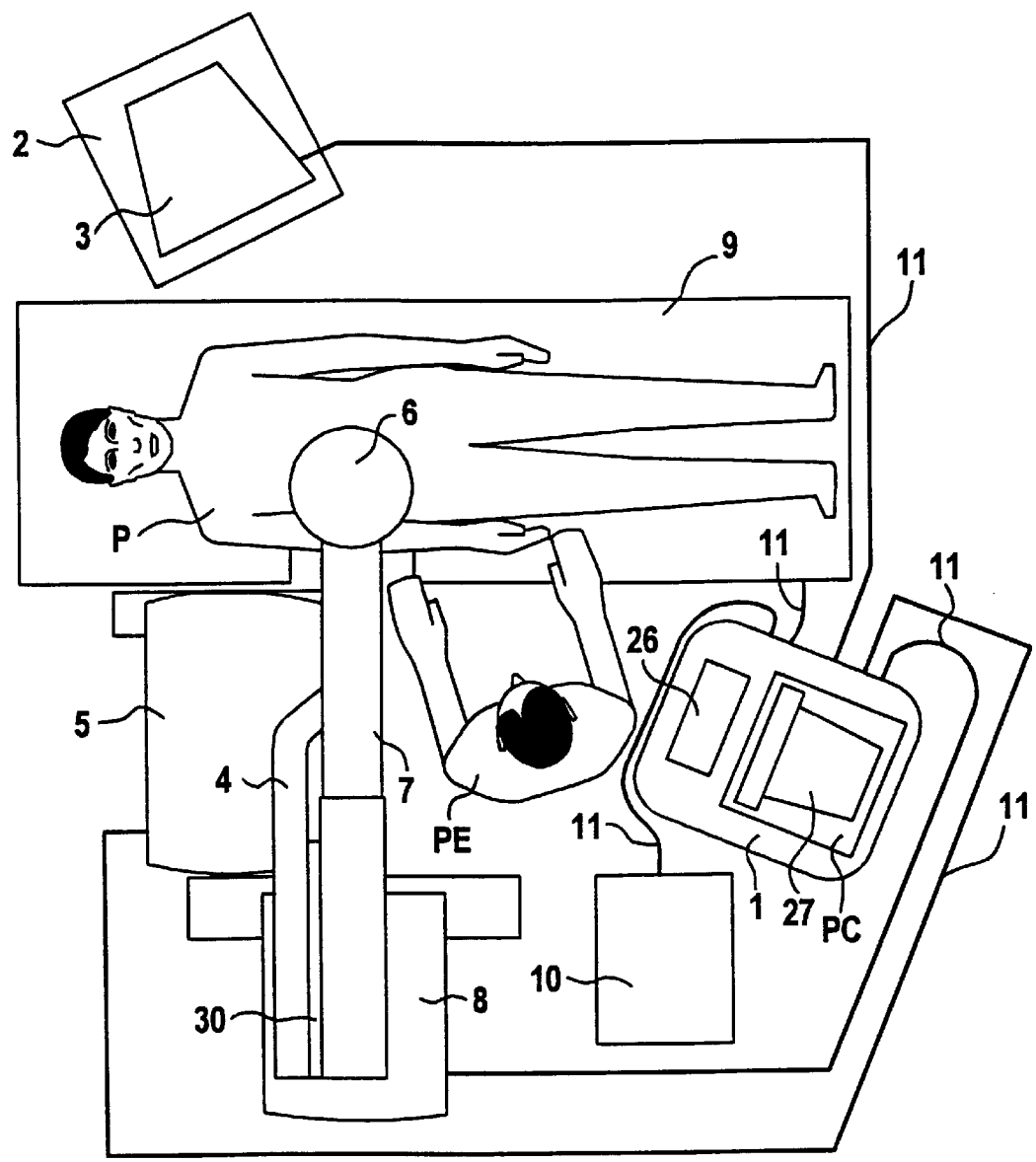
FIG. 1 shows an apparatus system according to the invention in the form of a workstation for lithotripsy.

FIG. 1 shows a plan view of an apparatus system according to the invention which, in the exemplary embodiment, is shown in the form of a medical apparatus system. The medical apparatus system has various medical apparatuses which are separately designed, can be operated independently of one another and form a medical workstation for the treatment of a patient P suffering from calculi, for example kidney stones. The workstation has a connection unit 1, to which are connected, in a releasable manner, the 30 individual medical apparatuses and a monitor 3 for the central display of information obtained by means of the medical apparatuses. The monitor is assigned to the connection unit 1 and is arranged on a trolley 2. In the case of the present workstation, the medical apparatuses, which are individually known, are a lithotripter 5, which has a shock wave source (not visible in FIG. 1) arranged on a holding arm 4 and serving to disintegrate the stones, a C-arm X-ray apparatus 8, which has a C-arm 7 provided with an X-ray source (not visible) and an X-ray receiver 6, a vertically and horizontally adjustable patient supporting table 9, and a diagnostic ultrasound apparatus 10 having an ultrasound head (not illustrated). The medical apparatuses 5, 8, 9, 10 (which because they are individually known need not be described in specific detail), can be operated independently of one another and independently of the connection unit 1 to which they are connected in the case of the present exemplary embodiment. The apparatuses 5, 8, 9, 10 each have, in a manner that is not specifically illustrated, a dedicated housing and/or a dedicated apparatus trolley, dedicated controllers and items of equipment for operating them as intended. In the case of the present exemplary embodiment, all the medical apparatuses with the exception of the patient supporting table 9 are of mobile design, in a manner that is not illustrated.

In the case of the present exemplary embodiment, the holding arm 4 of the shock wave source of the lithotripter S and the C-arm X-ray apparatus 8 are mechanically coupled to one another, in an releasable manner, via a mechanism 30 (not illustrated in specific detail) in such a way that the focus of the shock wave source (not visible) of the lithotripter 5 lies approximately in the path of the central ray of a pencil beam of X-rays emanating from the X-ray source (not visible) to the X-ray receiver 6 of the C-arm X-ray apparatus 8.

The C-arm X-ray apparatus 8 and the diagnostic ultrasound apparatus 10 of the medical apparatus system serve, in a known manner, to locate the kidney stones (not illustrated in FIG. 1) to be disintegrated in the body of the patient P.

The patient supporting table 9 and the C-arm X-ray apparatus 8, which is coupled to the lithotripter 5, are adjustable relative to one another, in a known manner, for the purpose of locating the kidney stones and for the purpose of setting the focus position of the shock wave source of the lithotripter 5 on the kidney stones. In this case, the shock wave source of the lithotripter 5 has, in a known manner, a central region into which the ultrasound head of the diagnostic ultrasound apparatus 10 can be introduced for location purposes.

Figure 2:
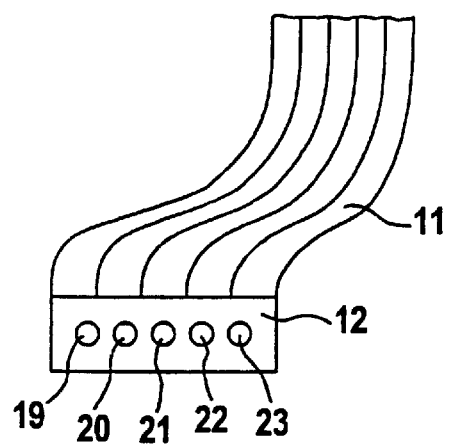
FIG. 2 shows a system lead with system connector, for use in the inventive apparatus system.

In order to locate the kidney stones in the body of the patient P by means of the C-arm X-ray 10 apparatus 8 and/or the diagnostic ultrasound apparatus 10 and in order to align the focus of the shock wave source of the lithotripter S with the kidney stones of the patient P, it is necessary for the lithotripter 5, the C-arm X-ray apparatus 8, the diagnostic ultrasound apparatus 10 and the patient supporting table 9 to exchange data with one another at least in part. For this purpose, the medical apparatuses 5, 8, 9 and 10 and also the monitor 3 are connected to the connection unit 1. The medical apparatuses 5, 8, 9, 10 and the monitor 3 are connected to the connection unit 1, in order to form the workstation, in each case via a system lead 11, which is routed from the medical apparatuses 5, 8, 9, 10 and the monitor 3 to the connection unit 1. A system lead 11 of one of the medical apparatuses 5, 8, 9, 10 and/or of the monitor 3, which system lead is illustrated as an example in FIG. 2, has a number of connecting cables, which are combined in the system lead 11, and a system connector 12 for the purpose of connecting the apparatus to the connection unit 1.

Figure 3:
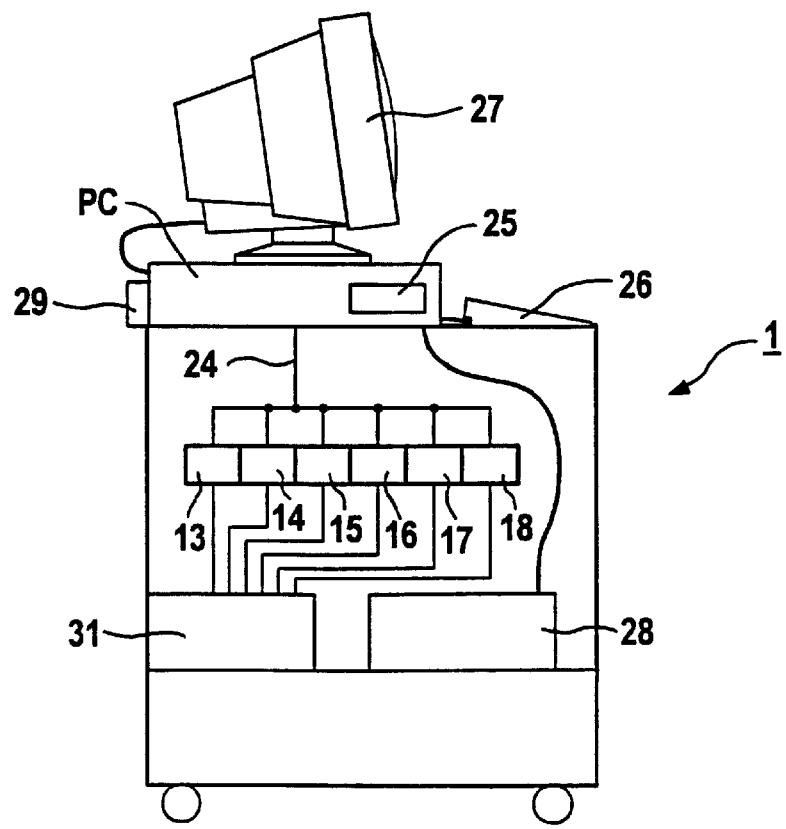
FIG. 3 shows the connection unit from FIG. 1.

As illustrated in FIG. 3, the connection unit 1 has corresponding plug devices 13 to 18 for accommodating the system connectors 12 of the system leads 11 of the medical apparatuses 5, 8, 9, 10 and of the monitor 3. Tn the case of the present exemplary embodiment, the system leads 11 have two connecting cables 19, 20 for the transmission power supply cables 22, 23 for power transmission. In the case of the present exemplary embodiment, all the medical apparatuses 5, 8, 9, 10 and the monitor 3 have such a system lead 11 provided with a system connector 12.

Figure 4:
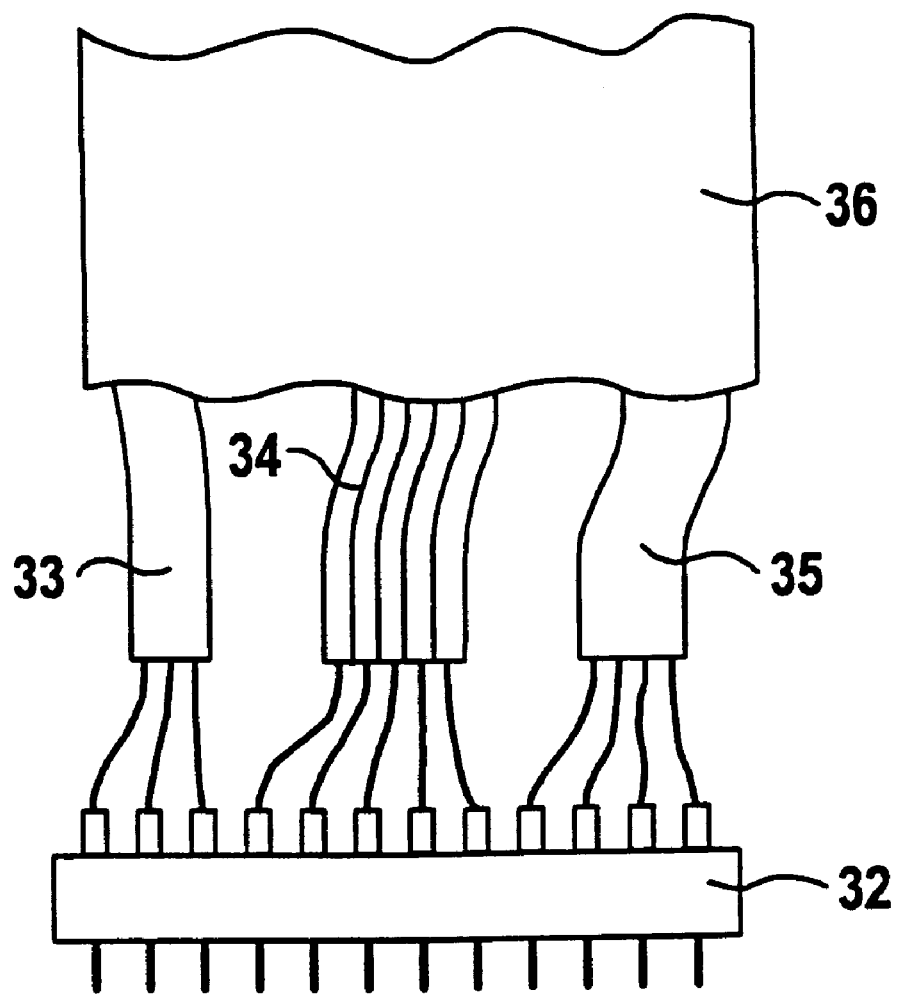
FIG. 4 shows another embodiment of a system connector for use in the inventive apparatus system.

The system lead and the system connector of a medical apparatus, however, need not necessarily be designed like the system lead 11 and the system connector 12. Rather, the system lead and the system connector may also have fewer or more than the five cables illustrated in FIG. 2, depending on the medical apparatus to be connected to the connection unit 1. A system connector 32, which is designed differently with respect to the system connector 12, is diagrammatically illustrated as an example in FIG. 4. The system connector 32 has a total of twelve connections, three cables combined in a lead 33 for the transmission of video signals being arranged at three connections, five cables combined in a lead 34 for the transmission of data being arranged at five connections and four cables combined in a lead 35 for power transmission being arranged at four connections. The leads 33 to 35 are finally combined to form a system lead 36.

In addition, the respective system leads and system connectors need not necessarily all be designed identically and have cables from each of the three categories, but rather may also be designed differently rom one another. For example, a system lead for the connection of a monitor can be provided just with video and power supply cables. Depending on the embodiment of the system connectors of the medical apparatuses 5, 8, 9, 10 and/or of the monitor 3, the plug devices 13 to 18 of the connection unit 1 must be of corresponding design. The number of plug devices in the case of the present exemplary embodiment is to be understood as being only by way of example. In other words, it is also possible for more or fewer than the six plug devices 13 to 18 depicted in FIG. 3 to be present on the connection unit 1.

In the case of the present exemplary embodiment, the connection unit 1 furthermore has a 5 control computer in the form of a personal computer PC, which is connected to the plug devices 13 to 18 via a communications bus 24. The connections of the plug devices 13 to 18 for the data cables 19, 20 of the system leads 11 or system connectors 12 are in this case routed to the communications bus 24 of the connection unit 1. The connections of the plug devices 13 to 18 for the power supply cables 22, 23 of the system leads 11 or system connectors 12 are routed to a power supply unit 31 of the connection unit 1, which supplies all the apparatuses 5, 8, 9, 10 and the monitor 3 with electrical power via the system leads 11. The connections of the plug devices 13 to 18 for the video cables 21 of the system leads 11 or system connectors 12 are connected to the PC in the case of the present exemplary embodiment, an illustration of the connections having been dispensed with for clarity.

In the case of the present exemplary embodiment, the PC of the connection unit 1 on the one 25 hand controls, via the communications bus 24, the data exchange between the medical apparatuses 5, 8, 9, 10 during the treatment of the patient P, which is carried out and monitored by a person PE. Additionally, the PC controls the exchange of video and documentation data between the PC and the medical apparatuses 5, 8, 9, 10 as well as the display of the information obtained by means of the medical apparatuses 5, 8, 9, 10 on the monitor 3 connected to the PC of the connection unit 1. The information may be, for example, image information obtained by means of the C-arm X-ray apparatus 8 or the diagnostic ultrasound apparatus 10 or, if appropriate, also position and status information of the medical apparatuses 5, 8, 9, 10. In this case, the information can be displayed successively or simultaneously, it being possible to effect the latter case by dividing the screen into different, even variable, areas.

However, for the purpose of data exchange, the medical apparatuses 5, 8, 9, 10 and the monitor 3 need not necessarily be connected to the PC via a communications bus, but rather may also be connected to suitable interfaces of the PC.

In addition, the data exchange between the medical apparatuses 5, 8, 9, 10 and the monitor 3 and also the data exchange between the PC and the medical apparatuses 5, 8, 9, 10 and the monitor 3 need not necessarily be controlled by the PC, but rather may also be effected independently of the PC via the communications bus 24.

In the case of the present exemplary embodiment, the PC of the connection unit 1 furthermore serves as documentation means, for which purpose the PC has electronic storage media in the form of a hard disk 25, known drives (not illustrated) for magnetic memories and input and output modules in the form of a keyboard 26, a monitor 27 and a printer 28. In this way, in the case of the present medical apparatus system, it is possible, at the same time as information obtained by means of the medical apparatuses 5, 8, 9, 10, for example image information from the C-arm X-ray apparatus 8, is displayed on the monitor 3, for patient and/or treatment data, for example, to be displayed on the monitor 27 of the connection unit 1, input, updated and stored and for findings to be printed out by the printer 28. At the same time, it is also possible for the information obtained by means of the medical apparatuses 5, 8, 9, 10 to be saved for example to the hard disk 25 or magnetic memory or to be printed out on the printer 28. Furthermore, the PC of the connection unit 1 may be connected, for example via a corresponding connection 29, to a bus system of a clinical data network, with the result that the patient and/or treatment data can even be retrieved from a central storage medium or be stored thereon.

The PC of the connection unit I can be replaced by an equivalent control computer which performs the functions of the PC. In addition, instead of one PC, it is also possible to provide a number of PCS or control computers which control or handle the data exchange, the display of information and the documentation and can communicate with one another.

Furthermore, it is possible, in principle, for the procedure for treating a patient P to be controlled centrally for example from the PC of the connection unit 1 or else from one of the medical apparatuses, for example the lithotripter 5.

Preferably, the PC or the control computer of the connection unit 1 is additionally able to identify apparatuses which are connected to the connection unit 1 in accordance with the plug & play principle, thereby rendering unnecessary any further measures on the part of an operator for the configuration of the workstation by logging medical apparatuses onto or off from the PC of the connection unit 1. An apparatus connected to the connection unit 1 is thus identified independently by the PC or control computer and, as far as the data exchange and power supply are concerned, is immediately ready for use.

Moreover, the monitor 3 for the central display 30 of the information obtained by means of the medical apparatuses need not necessarily be arranged on an adjustable trolley 2, but rather may also be arranged on a wall-, floor- or ceiling-mounted holding arm (articulated arm).

It thus becomes clear that a medical workstation can be constructed in a simple and modular manner, preceding from the connection unit 1, by connecting different, separately designed, medical apparatuses which can be operated independently of the connection unit 1. The connection unit 1, which preferably has a PC and a communications bus 24, in this case enables the data exchange between the individual apparatuses, the visualization of information obtained by means of the medical apparatuses, and the documentation of patient and/or treatment data, and ensures that the apparatuses are supplied with power. In this case, the connection unit 1 may be constructed as an apparatus trolley or else as a stationary unit. Equally, the medical apparatuses may also be designed as stationary units or mobile units.

By virtue of the fact that each apparatus of the medical system is in this case connected to the 15 connection unit 1 by only one system lead with connecting cables for the transmission of data, video data and power, the number of free connecting cables of a system of this type is greatly reduced. In this way, the construction of an apparatus system of this type is simplified and the risk of tripping over which is posed by the system leads is reduced considerably.

The apparatus system according to the invention was explained above using the example of a medical apparatus system for crushing concretions, kidney stones in the present case, in the body of a patient P. However, the medical apparatus system can also be used in pain therapy, osteo-restoration or for the treatment of tissue in the body of a patient, for example tumor tissue.

Furthermore, the apparatus system according to the invention is not restricted to medical fields of application.

We claim as our invention:

1. A medical apparatus system comprising:

a plurality of independently operable medical apparatuses;

a connection unit connectable to each of said medical apparatuses to form a medical workstation, in which said medical apparatuses are also independently operable of each other and independently operable of said connection unit;

each of said medical apparatuses having a system lead comprising a plurality of connecting cables connected to a system connector, and said connection unit having plug devices mating with said system connectors for connecting said medical apparatuses to said connection unit, with all electrical cables required to operate the medical apparatus being contained in the system lead for that medical apparatus.

2. A medical apparatus system as claimed in claim 1 wherein each of said connecting cables comprises cables selected from the group consisting of data cables, video cables and power supply cables.

3. A medical apparatus system as claimed in claim 1 wherein all of said plug devices, all of said connecting cables and all of said system connectors are identical.

4. A medical apparatus system as claimed in claim 1 wherein said connection unit comprises at least one communications bus.

5. A medical apparatus system as claimed in claim 1 wherein said connection unit comprises at least one control computer for controlling at least one of said medical apparatuses.

* * * * *